US008197864B2

(12) United States Patent
Antony

(10) Patent No.: US 8,197,864 B2
(45) Date of Patent: Jun. 12, 2012

(54) PREPARATION, PROCESS AND A REGENERATIVE METHOD AND TECHNIQUE FOR PREVENTION, TREATMENT AND GLYCEMIC CONTROL OF DIABETES MELLITUS

(75) Inventor: Merina Benny Antony, Ankamaly (IN)

(73) Assignee: Arjuna Natural Extracts, Alwaye (IN)

( * ) Notice: Subject to any disclaimer, the term of this patent is extended or adjusted under 35 U.S.C. 154(b) by 0 days.

(21) Appl. No.: 13/064,565

(22) Filed: Mar. 31, 2011

(65) Prior Publication Data

US 2011/0183020 A1    Jul. 28, 2011

Related U.S. Application Data

(60) Division of application No. 12/591,067, filed on Nov. 6, 2009, now Pat. No. 7,939,114, which is a division of application No. 12/081,849, filed on Apr. 22, 2008, now Pat. No. 7,635,495, which is a division of application No. 11/808,381, filed on Jun. 8, 2007, now Pat. No. 7,378,113, which is a division of application No. 11/418,250, filed on May 5, 2006, now Pat. No. 7,255,886, which is a continuation of application No. PCT/IN2004/000019, filed on Jan. 28, 2004.

(51) Int. Cl.
    *A61K 36/00* (2006.01)
(52) U.S. Cl. .................. 424/725; 424/774
(58) Field of Classification Search .......... None
    See application file for complete search history.

(56) References Cited

U.S. PATENT DOCUMENTS

| 6,252,057 | B1 | 6/2001 | Brady et al. |
| 6,632,461 | B1 | 10/2003 | Slimak |
| 2002/0136777 | A1 | 9/2002 | Choi et al. |
| 2002/0172743 | A1 | 11/2002 | Chawan |
| 2004/0002423 | A1 | 1/2004 | Ohnogi et al. |
| 2005/0031772 | A1 | 2/2005 | Gaedcke et al. |

FOREIGN PATENT DOCUMENTS
KR    354912 B    10/2002

OTHER PUBLICATIONS

Ramachandran, A, Snehalatha, C, Latha, E, Vijay, V, Viswanathan, M, Rising prevalence of NIDDM in an urban population in India, Diabetologia, 40:232-237 (1997).
Rao, RM, Salem, FA, Gleason-Jordan, I, Antidiabetic effects of a dietary supplement "pancreas tonic," J. Natl. Med. Assoc., 90:614-618 (1998).
King, H, Aubert, RE and Herman, WH, Global Burden of Diabetes, 1995-2025, Prevalence, Numerical Estimates, and Projections, Diabetes Care, 21(9):1414-1431 (1998).
Zhou, J, Wang, X, Pineyro, MA and Egan, JM, Glucagon-like Peptide 1 and Exendin-4 Convert Pancreatic AR42J Cells Into Glucagon- and Insulin-Producing Cells, Diabetes, 48:2358-2366 (Dec. 1999).
Xu, G, Stoffers, DA, Habener, JF and Bonner-Weir, S, Exendin-4 Stimulates Both β-Cell Replication and Neogenesis, Resulting in Increased β-Cell Mass and Improved Glucose Tolerance in Diabetic Rats, Diabetes, 48:2270-2276 (Dec. 1999).
American Diabetes Association, Type 2 Diabetes in Children and Adolescents, Diabetes Care, 23(3):381-389 (Mar. 2000).
Zimmet, P, Alberti, KGMM and Shaw, J, Global and Societal Implications of the Diabetes Epidemic, Nature, 414:782-787 (Dec. 13, 2001), Macmillan Magazines Ltd.
Nahar, N, Mosihuzzaman, M, and Khan, SH, Determination of Free Sugars in Plant Materials having Antidiabetic Activity, Dhaka Univ. J. Sci., 46(1):167-170 (Jan. 1998).
Mosihuzzaman, M, Nahar, N, Ali, L, Rokeya, B, Azad Khan, AK, Nur-E-Alam, M and Nandi,RP, Hypoglycemic Effects of Three Plants from Eastern Himalayan Belt, Diabetes Research, 26(33):127-138 (1994), Teviot-Klimpton Publications.
Basualdo, I, Zardini, E, and Ortiz, M, Medicinal Plants of Paraguay: Underground Organs, Economic Botany, 45(1):86-96 (1991), New York Botanical Garden, Bronx, NY 10458.
Anaga, AO, Njoku, CJ, Ekejiuba, ES, Esiaka, MN, and Asuzu, IU, Investigations of the Methanolic Leaf Extract of *Costus afer.* Ker for Pharmacological Activities in vitro and in vivo, Phytomedicine, 11:242-248 (2004), Elsevier.
Griffin, BW, Chandler, ML, and DeSantis, L, Prevention of Diabetic Cataract and Neuropathy in Rats by Two New Aldose Reductase Inhibitors, Invest Ophthal. Vis. Sci. vol. 25 (Supplement), p. 136, ARVO Abstract No. 36 (Mar. 1984).
Katzung, BG, (editor), Basic and Clinical Pharmacology, International Edition (8th Edition), pp. 723-730 (2001), Appleton & Lange.
Harris, MI, Flegal, KM, Cowie, CC, Eberhardt, MS, Goldstein, DE, Little, RR, Wiedmeyer, MS, Bryd-Holt, DD, Prevalence of Diabetes, Impaired Fasting Glucose, and Impaired Glucose Tolerance in U.S. Adults, Diabetes Care, 21(4):518-524 (Apr. 1998).
Two (2) pages of International Search Report dated Aug. 11, 2005, for PCT/IN04/00019.

*Primary Examiner* — Qiuwen Mi
(74) *Attorney, Agent, or Firm* — Jyoti C. Iyer

(57) ABSTRACT

A medicinal preparation, a process, a nutritional composition and regenerative and insulin potentiating method for humans and also for mammals for prevention, treatment and management/glycemic control of diabetes mellitus by obtaining optimum glucose level in blood, by administering an extract of *Costus pictus* to produce above effect in a dose of 500-2000 mg/day in humans and 50-200 mg/kg/day in rats. A method for treating hyperglycemia in a patient by administering a medicinal preparation of *Costus pictus D. Don.* A method for long term management of diabetes by avoiding the problems associated with tight control of blood glucose concentrations, i.e., hypoglycemia tolerance and seizures, while simultaneously avoiding the problems associated with conventional moderate control of blood glucose concentrations, i.e., pathological complications associated with hyperglycemia, such as nephropathy, retinopathy, etc. The medicinal preparation further affords an insulin potentiating action in addition to decreasing blood glucose and/or glycosylated hemoglobin levels.

12 Claims, 8 Drawing Sheets

PREPARATION, PROCESS AND A REGENERATIVE METHOD AND TECHNIQUE FOR PREVENTION, TREATMENT AND GLYCEMIC CONTROL OF DIABETES MELLITUS

RELATED APPLICATIONS

This application is a divisional of U.S. application Ser. No. 12/591,067(now issued as U.S. Pat. No. 7,939,114), filed Nov. 6, 2009, which is a divisional of U.S. application Ser. No. 12/081,849, filed Apr. 22, 2008 issued as U.S. Pat. No. 7,635,495, which is a divisional of U.S. application Ser. No. 11/808,381, filed Jun. 8, 2007, which issued as U.S. Pat. No. 7,378,113, which is a divisional of U.S. application Ser. No. 11/418,250, filed May 5, 2006, which issued as U.S. Pat. No. 7,255,886 on Aug. 14, 2007, which is a continuation of PCT Application Serial No. PCT/IN2004/000019, filed Jan. 28, 2004. The entire disclosures of the prior applications U.S. application Ser. Nos. 12/591,067, 12/808,381 and 11/418,250 and International Application No. PCT/1N2004/00019 are hereby incorporated by reference.

FIELD

This disclosure relates to an innovative and path-breaking technique that treats Diabetes mellitus and to obtain optimum glycemic control in type I and type II diabetic patients. The disclosure also provides an eco-friendly method and manner of extracting the plant *Costus pictus D. Don.*

Syn: *Costus mexicanus.*

This disclosure provides a method of treating Diabetes mellitus to obtain optimum glycemic level in blood.

BACKGROUND

References

The following papers provide useful background information, for which they are incorporated herein by reference in their entirety.
1) U.S. Pat. No. 6,632,461, issued Oct. 14, 2003 "Use of tropical root crops in effective intervention strategies for treating difficult and complex cases and chronic diseases" by Slimak.
2) U.S. Pat. Application 20040002423 A1, Jan. 1, 2004, "Remedies" by Ohnogi, Hiromu.
3) Zimmet P, Alberti K G, Shaw J. Global and societal implications of the diabetes epidemic. Nature 2001; 414: 782-787.
4) King H, Aubert R E, Herman W H. Global burden of Diabetes, 1995-2025: prevalence, numerical estimates, and projections. Diabetes Care 1998; 21: 1414-1431.
5) Ramachandran A, Snehalatha C, Latha E, Vijay V, Viswanathan M. Rising prevalence of NIDDM in an urban population in India. Diabetologia 1997; 40: 232-237.
6) Harris M I, Fleggal K, Cowie C, Eberhardt M S, Goldstein D E, Little R R, Wiedmeyer H M, Byrd-Holt D D. Prevalence of diabetes, impaired fasting glucose and impaired glucose tolerance in U.S adults. The Third National Health and Nutrition Examination Survey, 1988-1994. Diabetes Care 1998; 21: 518-524.
7) Type 2 Diabetes in children and adolescents. American Diabetes Association. Diabetes Care 2000; 23: 381-389.
8) Katzung G. Basic and Clinical Pharmacology, International Edition, (8th Edition) edited by Bertraram, Pages 2001, 723-730
9) National Health Interview Survey and (1999-2001) National Health and National Examination Survey estimates projected to year: 2002.
10) Grifin B. W. Prevention of diabetic cataract and neuropathy in rats by two new aldose inhibitors. Invest Ophthal. Vis. Sci. (1984) 25:136.
11) Rao R M, Salem F A, Gleason-Jordan I. Antidiabetic effects of dietary supplement "Pancreas Tonic" J. Natl. Med. Assoc., (1998) 90:614-618.
12) Asatoor A M & King E J, Simplified colorimetric blood sugar method, Process Biochem. 1954 Jan. 16; 56 ($325^{th}$ meeting).
13) Zhou, J. et al., Diabetes, 1999; 48 (12): 2358-2366.
14) Xu, G. et al., Diabetes, 1999; 48 (12):2270-2276.

BACKGROUND

In this section, we discuss several aspects of related work, including background and conventional technologies.

Globally, the number of people with diabetes is expected to rise from the current estimate of 150 millions to 220 millions in 2010 and 300 millions in 2025. The prevalence is increasing in the developing countries such as India, particularly in urban areas. The estimated number of diabetes patients in India was 19.4 million in 1995 and are expected to be 57.2 million in 2025 (W.H.O). In the United States, it is estimated that as of 2002, 18.2 million people (6.3% of the total population) were diabetic. About 2.06 lakhs of people under 20 years of age have diabetes (0.25% of all people in this age group). Approximately one in every 400-500 children and adolescents has Type-1 diabetes. In the age group of 20 years or older, 18 million (8.7% in men and 9.3% in women) have diabetes. In people above the age of 60 years, 8.6 million (18.3% of all people in this age group) have diabetes.

There are mainly two types of diabetes. Type-1 diabetes which was previously called insulin dependent diabetes mellitus (IDDM) or juvenile-onset diabetes. This develops when the body's immune system destroys pancreatic beta cells (β-cells), which are the only cells in the body that make the hormone insulin that regulates blood glucose level. The pancreas comprises two glandular tissues, one, is a collection of cells that form the exocrine function of the pancreas where these exocrine cells synthesize and release digestive enzymes into the intestine; the second tissue comprises the endocrine function of the pancreas which synthesize and release hormones into the circulation. Of prime importance for the endocrine function of the pancreas are the beta cells. These cells synthesize and secrete the hormone insulin. The hormone insulin plays a vital role in maintaining normal physiological glycemic levels. There are molecules that are effectors of the endocrine cells of the pancreas. Glucoincretins are an example of such molecules. Incretins potentiate glucose-induced insulin secretion from the pancreas. In Type-1 diabetes there is decreased insulin production and the circulating insulin level is very low. Type-1 diabetes usually strikes children and young adults, although the disease onset can occur at any age. It accounts for 5-10% of all diagnosed cases of diabetes. Risk factors for Type-1 diabetes may include autoimmune, genetic, and environmental factors.

Type-II diabetes was previously called non-insulin dependent diabetes mellitus (NIDDM) or adult onset diabetes. It usually begins as insulin resistance, a disorder in which the cells of the body fails to respond to insulin properly. As the need for insulin rises, the pancreas gradually loses its ability to produce insulin. Beta cells of pancreatic islets are dysfunctional. Type-II diabetes is associated with older age group, obesity, family history of diabetes, history of gestational diabetes, impaired glucose metabolism, physical inactivity, and race/ethnicity. In recent years, Type-II diabetes is increasingly being diagnosed in children and adolescents. Type II diabetes is the predominant form of diabetes world wide, accounting for 90% of cases globally. An epidemic of Type II diabetic patients is underway in both developed and developing countries, although the brunt of the disorder is felt disproportionally in non-European populations, especially in India.

Type II diabetes has become one of the world's most important public health problems. It is currently thought to occur in genetically predisposed individuals, who are exposed to a series of environmental influences that precipitate the onset of clinical disease. Sex, age and ethnic background are important factors in determining the risk for the development of Type II diabetes. The disorder is more common in the females.

Age is also an important factor. Type II diabetes has been viewed in the past as a disorder of aging with an increasing prevalence with age. This remains true today. However, a disturbing trend has become apparent in which the prevalence of obesity and type II diabetes in children is rising dramatically. In the past, it was believed that the overwhelming majority of children with diabetes had type 1 diabetes, with only 1-2% children considered to have type II or other rare forms of diabetes. Recent reports suggest that as many as 8-45% of children with newly diagnosed diabetes have non-immune-mediated-diabetes. The majority of these children have type II diabetes, but other types are also being identified. Normal insulin secretory function is essential for the maintenance of normal glucose tolerance, and abnormal insulin secretion is invariably present in patients with type II diabetes.

Gestational diabetes is a form of glucose intolerance that is diagnosed in some women during pregnancy. It is more common among obese women and women with a family history of diabetes. During pregnancy, gestational diabetes requires treatment to normalize maternal glucose level in order to avoid complications in the infant. After pregnancy, 5-10% of women with gestational diabetes are found to have type-II diabetes. Women who have had gestational diabetes have a 20% to 50% chance of developing diabetes in the next 5-10 years.

Other specific types-of diabetes result from specific genetic conditions (such as maturity onset diabetes of youth), surgery, drug-induced, malnutrition, infections, and other illnesses. Such types account for 1-5% of all diagnosed cases of diabetes.

Type-1 diabetic patients have virtually no functional β-cells, can neither respond to variations in circulating glucose nor maintain a basal secretion of insulin, and the treatment principle is to achieve blood glucose concentration as close to normal as possible to reduce the risk of diabetic complications. Previous proposals for treatment include application of exogenous bioactive Glucagon-like peptide-1 (7-36) amide ("GLP-1") or its analogs, to either stimulate islet cell regeneration in vivo, or to obtain pancreatic cells from diabetes mellitus patients and to treat such cells ex vivo in tissue culture using bioactive GLP-1. This ex vivo treatment was considered to facilitate regeneration and/or differentiation of Islet cells which could then synthesis and secrete insulin or glucagon.

However, such a treatment regime requires the enteral or parenteral application of bioactive GLP-1 to patients, including the possibility of surgery. It is one aspect to obviate the need for surgical treatment, enteral or parenteral applications of bioactive GLP-1.

There are two types of treatments depending on the patient's condition. Intensive therapy—with insulin administration by insulin pump or 3-4 or more daily injections with a goal to achieve blood glucose levels between 70-120 mg/dl before meals, less than 180 mg/dl after meals and weekly 3 AM measurement greater than 65 mg/dl and HbA1C (glycosylated haemoglobin) value within the normal range (6.05% or less).

Conventional therapy consists of one or two daily injection of insulin including mixed intermediate and rapid acting insulins daily, with self monitoring of urine and blood glucose. Intensive therapy gives good glycemic control and decreases the risk of retinopathy by 47%, microalbuminuria by 34%, while secondary intervention causes 43% protection.

According to the American Diabetes Association's revised guidelines for 2002, the goal of therapy is to achieve average prepandial plasma glucose concentration in the range of 90-130 mg/dl, average bedtime plasma glucose values between 110-150 mg/dl and HbA1C values less than 7%.

In Type II diabetic patients, beta cells (β-cells) of the Islets of Langerhans are intact, but dysfunctional. They are not secreting enough insulin needed, there is also insulin resistance and the cells do not respond to insulin. The major predisposing factor is obesity. Hence treatment is initiated with dietary changes and exercise and if the patient does not improve, drugs are prescribed. The revolution in the treatment of Type II diabetes since 1995 has been the release of multiple new classes of drugs that independently address different pathophysiological mechanisms that contribute to the development of diabetes.

The available oral anti-diabetic drugs can be divided by their mechanism of action as shown in Table 1.

TABLE 1

Orally administered anti-diabetic drugs.

| Class | Approved Drugs | Mechanism Of action | Limitations |
|---|---|---|---|
| Sulphonylureas (Insulin secretagogues) | 2 ($2^{nd}$ gen) 4 ($1^{st}$ gen) | Act on pancreatic β Cells to release insulin | Insulin resistance |
| Biguanides (Insulin sensitizers) | only one (Metformin) | decrease glucose release by liver improves insulin sensitivity | lactic acidosis |
| Thiazolidine-diones (Insulin sensitizers) | only one (Glitazones) | diminish insulin resistance & improve insulin sensitivity | fluid retention weight gain hypoglycemia, cannot be used in presence of heart & liver disease |
| ∝Glucosidase inhibitors | 2 (Acarbose, Miglitol) | slow the absorption of carbohydrates | flatulence, diarrhoea, abdominal pain |

Even though a variety of modern drugs are available for the treatment of diabetes mellitus, as in above table none of them are without side effects. Insulin even though very potent, remains the drug of choice for Type-1 diabetics and also for type-II diabetics who do not obtain glycemic control with oral anti-diabetic drugs. The main disadvantage of insulin is that it is not orally effective because it is destroyed upon oral administration, and hence has to be given by injection.

BACKGROUND ART

Diabetes mellitus was known to ancient Indians as early as sixth century B. C. Charaka in his "Charaka Samhita" has mentioned the sweetness of urine in addition to polyuria. The Indian physician Susruta in 500 A.D described the disease as "Madhumeha" meaning rain of honey, (due to the phenomenon of attracting ants near the urine of a diabetic patient) with symptoms of foul breath, voracious appetite and langour. Other early Indian writings like Astanga-hrayda, Bhava-prakasa, Madhav-nidana etc. have also described diabetes.

In ancient traditional medicine, the treatment of diabetes was attempted with different indigenous plants or their combinations administered orally. These anti-diabetic agents can be divided into two groups according to their source of origin: vegetable or herbal preparations and mineral preparations. Vegetable or herbal agents administered as "asawas" and "arishtas' constitute the majority of Indian indigenous anti-diabetic drugs. Mineral preparations are given as "Bhasmas" are comparatively fewer. The main stay of treatment was dietary therapy.

The high costs of modern treatment of diabetes indicate a great need for the development of alternative strategies for the prevention and treatment of diabetes. Approximately 90% of the population in rural areas of developing countries still relies on traditional medicines for their primary health care.

Since antiquity, diabetes has been treated with plant medicines. More than 1200 species of plants have been screened for anti-diabetic activity on the basis of Ethanopharmacology or on random basis. These products range from marine algae and fungi to phylogenetically advanced classes of plants. There are about 200 pure compounds from plant sources with reported blood sugar lowering effect. Recent scientific investigations on animals and humans had confirmed the efficacy of many of these preparations, some of which are very effective, relatively non-toxic.

They are broadly divided into (a) those used as part of diet (b) those used as herbal drugs. Onion (*Allium cepa*), Garlic (*Allium sativum*), Fenugreek—(*Trigonella foenumgraecum*), *Momordica charantia* (bitter gourd/Kaippaka), *Coccinia grandis* (Linn), *Cinnamomum tamela* (Indian bay leaf), *Muraya koengei* leaves and *Cyamopsis tetragonoloba* (Cluster beans) are vegetables which form a part of diabetic diet. *Emblica officinalis* (Indian goose berry, amla), *Curcuma longa* (Turmeric), *Gymnema sylvestre* (Chakkara kolli), *Pterocarpus marsupium* (Venga) etc are some of herbal plants, found to have antidiabetic properties.

Many more herbs exhibit anti-diabetic action, but they have not been studied systematically. Unlike what was happening a few decades ago, anti-diabetic herbal formulations are marketed now in plenty in the form of powders, tablets, capsule and liquid preparations. Most of these have not undergone controlled clinical trials. Usually herbs with reputed anti-diabetic activity as documented in standard ayurvedic books or knowledge gained from experienced ayurvedic practitioners are taken up and mixtures are prepared with arbitrary dosage. Since most of these are non-toxic it is not causing much harm. It is true that some of these preparations are effective.

Hypoglycemic actions of some of the herbs with reputed use in the traditional system of medicine, Ayurveda, and used by the local Ayurvedic practitioners were reviewed with particular reference to the family 'Zingiberaceae.' *Curcuma longa* has been used in Indian and Chinese systems of medicine for a long time. The dried rhizome, commonly known as turmeric, is used for culinary purposes and is incorporated into many ayurvedic preparations. Turmeric mixed with amla (*Emblica officinalis*) fruit powder is used in the form of tablets for the treatment of Diabetes. Ginger, which belongs to the family Zingiberaceae, is also a rhizome. The fresh rhizome is used as a spice and in the preparations of curries. Ginger is also used as a dried powder for many Ayurvedic preparations, including those for the treatment of diabetes.

Interacting defects in muscle, liver, adipose tissue and pancreas, generate the pathogenic milieu that results in diabetes. Various classes of oral antihyperglycemic agents are currently available that target the different pathologic factors contributing to diabetes, for example, α-glucosidase inhibitors that delay intestinal carbohydrate absorption, biguanidines that target hepatic insulin resistance, insulin secretagogues that increase pancreatic insulin secretion, thiozolidonediones as insulin sensitizers to target adipocyte and muscle insulin resistance, and intestinal lipase inhibitors to inhibit fat absorption and promote weight loss in obese patients. A large number of plant-derived medications have also been described to effect glycemic control. However, none of these address the various aspects of diabetes concurrently, namely, control of blood sugar, regeneration of the beta cells of pancreas resulting in increased secretion of insulin, reducing insulin resistance, and correcting the decreased hepatic glycogen synthesis.

For this study, I selected an ornamental plant of the family Costaceae known as *Costus pictus D. Don,* which formerly belonged to the family Zingiberaceae and resembles ginger and turmeric plants but for the fact that the above said ornamental plant is not being used in any of the oriental treatment regimen for medicinal purpose, particularly for diabetes.

I hypothesized that since plants of the family Zingiberaceae, like turmeric are propagated as anti-diabetics, some other plants of the same family Zingiberaceae might be effective in the management of Type I and Type II diabetes.

SUMMARY

The disclosed teachings provide an extract of *Costus pictus D. Don.* The disclosure provides a preparation containing an extract of *Costus pictus D. Don* selected from a group consisting of a medicinal preparation, a nutritional composition, and combinations thereof.

The disclosure provides a pharmaceutical composition of an extract of *Costus pictus D. Don.* The disclosure provides a dosage form of an extract of *Costus pictus D. Don.* The disclosure provides a dosage form of an extract of *Costus pictus D. Don* for oral administration. Dosage forms of the extract are selected from the group consisting of a capsule, tablet, granule, sachet, powder, paste, ointment, infusion, injection, ampoule, solution, suspension, emulsion, pill, sustained release formulation and combinations thereof.

The disclosure provides a method of treatment of diabetes mellitus by administering an extract of *Costus pictus D. Don* to a mammal. Mammals include streptozotocin induced diabetic rats and humans. The method of treatment of diabetes mellitus includes administering a dose of about 50 mg/kg/day to about 200 mg/kg/day of an extract of *Costus pictus D. Don* to the streptozotocin induced diabetic rat. The method of treatment of diabetes mellitus includes administering a dose of about 500 mg/day to about 2000 mg/day of an extract of *Costus pictus D. Don* to a human in need of treatment, prevention or management of diabetes.

The disclosure provides a method of management of diabetes in a mammal by administering an extract of *Costus pictus D. Don.*

The disclosure provides a method of treatment, prevention or management of diabetes in a mammal by administering an extract of *Costus pictus D. Don.*

The disclosure provides a method of inducing hypoglycemia in a mammal for treatment, prevention or management of diabetes in the mammal by administering an extract of *Costus pictus D. Don* to the mammal.

The disclosure provides a method for regenerating beta cells of pancreatic islets in a mammal for treatment, prevention or management of diabetes in the mammal by administering an extract of *Costus pictus D. Don* to the mammal.

The disclosure provides a method for increasing the capacity of insulin producing cells in a mammal for the treatment, prevention or management of diabetes in the mammal by administering an extract of *Costus pictus D. Don*, whereby the endogeneous insulin producing cells of the mammal become more effective insulin producers.

The disclosure provides a method for increasing the capacity of insulin producing cells in a mammal for the treatment, prevention or management of diabetes in the mammal by administering an extract of *Costus pictus D. Don*, whereby damaged beta cells present in the pancreas regenerate into insulin producing cells.

The disclosure provides a method of controlling normal liver glycogen in a mammal for the treatment, prevention or management of diabetes in the mammal by administering an extract of *Costus pictus D. Don*.

The disclosure provides a method of preparing an extract of *Costus pictus D. Don* including:

collecting a starting material comprising *Costus pictus D. Don*; and treating the starting material with low molecular weight alcohols, low molecular weight alcohols mixed with water, halogenated hydrocarbons, organic ethers, low molecular weight esters, other organic solvents, low molecular weight ketones, water and combinations thereof to prepare the extract, wherein the starting material comprises a fresh whole plant of *Costus pictus D. Don*, fresh leaves of *Costus pictus D. Don*, dried leaves of *Costus pictus D. Don*, or combinations thereof.

The disclosure provides a method of preparing an extract of *Costus pictus D. Don* including:

collecting a starting material comprising *Costus pictus D. Don*;

refluxing the starting material with a first low molecular weight alcohol to prepare a mixture I;

filtering the mixture I to prepare a filtrate I and a residue I;

concentrating the filtrate I to prepare a concentrate I; and drying the concentrate I to prepare a fraction I, wherein the starting material comprises a fresh whole plant of *Costus pictus D. Don*, fresh leaves of *Costus pictus D. Don*, dried leaves of *Costus pictus D. Don*, or combinations thereof, and wherein the fraction I is designated as the extract.

The disclosure provides a method of preparing an extract includes collecting fresh leaves of *Costus pictus D. Don*, cleaning the fresh leaves to prepare cleaned leaves, drying the cleaned leaves to prepare dried leaves, powdering the dried leaves to prepare a dried powder, and refluxing the dried powder with a first low molecular weight alcohol to prepare the extract.

BRIEF DESCRIPTION OF THE DRAWINGS

The above objectives and advantages of the disclosed teachings will become more apparent by describing in detail preferred embodiments thereof with reference to the attached drawings in which.

DETAILED DESCRIPTION

Figure 1:
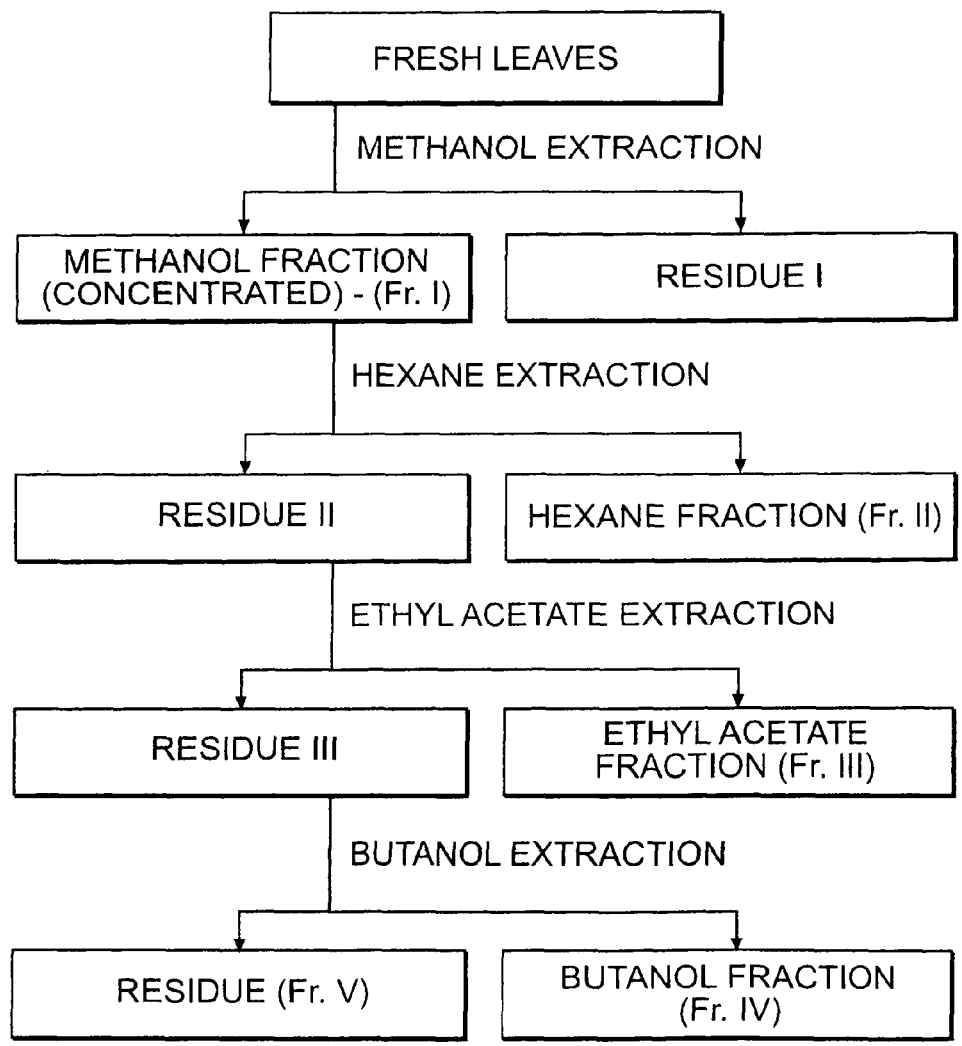
FIG. 1 shows a procedure to prepare one or more extracts from fresh leaves of *Costus pictus D. Don*.

The present invention relates to the use of a new plant extract in the treatment of diabetes mellitus. Diabetes mellitus is a group of metabolic disorders characterized by chronic hyperglycemia due to relative insulin deficiency, resistance or both. There is defect in insulin production, insulin action or both. The disclosure provides an innovative method and manner of preparing a unique medicinal preparation from *Costus pictus D. Don* that can be administered for prevention, treatment and optimum glycemic control of diabetes mellitus in humans and mammals. The disclosure provides an extract of *Costus pictus D. Don*. The disclosure provides a medicinal preparation of *Costus pictus D. Don*. The disclosure provides a nutritional composition *Costus pictus D. Don*. The disclosure provides combinations of medicinal preparation and nutritional composition of *Costus pictus D. Don*.

Methods to control blood glucose concentration by moderate administration of the disclosed medicinal preparation are disclosed. In appropriate proportions and with right techniques the medicinal preparation can be administered to regenerate beta cells of pancreatic islets. An innovative extraction of this innovative preparation administered therapeutically deploying an innovative manner and method effectively controls glycogen level in the liver of mammals and humans.

The disclosure provides an extract of *Costus pictus D. Don*, which addresses the various aspects of diabetes concurrently, namely, control of blood sugar, regeneration of the beta cells of pancreas resulting in increased secretion of insulin, reducing insulin resistance, and correcting decreased hepatic glycogen synthesis. A key aspect of the present invention, thus, is diabetes management. Glycogen control forms one aspect of this management. The disclosure provides a composition from *costus* which possesses sufficient novelty by favorably modifying the different aspects of the disease, simultaneously.

The disclosure teaches an innovative and path breaking technique to treat Diabetes mellitus by obtaining optimum glycemic control in blood. The disclosure teaches a plant extract in the form of pharmaceutical compositions and therapeutically (or prophylactically) effective amount of the compositions that is also pharmaceutically acceptable. The carrier and composition are produced under good laboratory practices conditions. The pharmaceutical preparation is ideally selected such that it suits the mode of administration, in accordance with conventional practice.

The preparation, if desired, can also contain minor amounts of wetting/emulsifying agents or pH buffering agents. In addition, the preparation can be a dosage form such as a liquid solution, suspension, emulsion, tablet, pill, capsule, sustained release formulation, powder, paste, ointment, sachet, ampoule, injection, infusion or combinations thereof.

Further, the compositions can be formulated in accordance with methods that are well known in the art of pharmaceutical composition and can be suitably adapted for intramuscular/subcutaneous/intravenous administration to human beings. Generally, the ingredients are supplied either separately or mixed together in unit dosage form, for example, as a dry lyophilized powder or water free concentrate in a hermetically sealed container such as an ampoule or sachet indicating the quantity of active compound. Where the composition is to be administered by infusion, it can be dispensed with an infusion bottle containing sterile pharmaceutical grade water, saline or dextrose/water. Where the composition is administered by injection, an ampoule of sterile water for injection or saline can be provided so that the ingredients may be mixed just prior to administration. Finally, compositions of the invention can be formulated as neutral or salt forms.

The amount of the invention's composition, which will be effective in the treatment of a particular disorder or condition, can be determined by standard clinical techniques. In addition, in vitro and/or in vivo assays may optionally be employed to help identify optimal dosage ranges. The precise dose to be employed in the formulation will also depend on the route of administration and the seriousness of the disease or disorder. The dose should be decided according to the judgment of the practitioner taking into consideration each patient's circumstances.

The disclosure provides a method and technique of treatment, prevention and/or management of diabetes wherein a hypoglycemically effective medicinal and/or nutritional preparation of *Costus pictus D. Don* can be administered to humans. The disclosure provides an effective treatment for controlling glycogen levels in the liver of diabetic mammals and humans. In an exemplary method the preparation is administered orally. The disclosure teaches a method and technique of administering the preparation of *Costus pictus D. Don* in the dosage of 500 mg-2000 mg/day for controlling type I and type II diabetics in human beings in the form of capsules, tablets, granules, sachets, powder and such other variations that may become available in future to fulfill the objectives of treatment, management or prevention of diabetes.

An ideal dosage includes administration of about 500 mg/day to about 2000 mg/day of an extract of *Costus pictus D. Don* to a mammal in need thereof for treatment, management or prevention of type I or type II diabetes. Other dosages include administration of about 50 mg/day to about 200 mg/day to a mammal in need thereof. In some embodiments, the method of treatment of diabetes mellitus includes administering a dose of extract of about 50 mg/kg/day to about 200 mg/kg/day to a streptozotocin induced diabetic rat. In some embodiments of the method of treatment of diabetes mellitus, a dose of extract of ranging from about 500 mg/day to about 2000 mg/day is administered to a human. In exemplary method of treatment of diabetes mellitus, the extract is administered at a dose ranging from about 500 mg/day to about 2000 mg/day to a diabetic patient. In some embodiments of the method of prevention of diabetes mellitus, a dose of the extract ranging from about 500 mg/day to about 2000 mg/day is administered to a human. In some embodiments of the method of management of diabetes mellitus, a dose of the extract of about 500 mg/day to about 2000 mg/day is administered to a human.

The extract can be administered to a mammal for a method of preventing diabetes. The extract can be administered to a mammal for a method of management of diabetes. In an exemplary method the extract is administered orally. In an exemplary method, the method of management of diabetes includes glycemic control. In an exemplary method, the method of management of diabetes includes regeneration of the beta cells of pancreas. In an exemplary method, the method of management of diabetes includes enhancing the capacity of pancreatic beta cells by causing endogeneous insulin producing cells to become more effective insulin producers. In an exemplary method, the method of management of diabetes includes enhancing hepatic glycogen synthesis from endogenous glucose. In an exemplary method, the method of management of diabetes includes reduced insulin resistance. In an exemplary method, a hypoglycemically active medicinal preparation is administered to humans for management of diabetes. In an exemplary method, a hypoglycemically active medicinal preparation is administered to humans for treatment of diabetes. The extract can be administered to a mammal for a method of treatment of diabetes. The extract can be administered to a mammal for a method of inducing hypoglycemia. The extract can be administered to a mammal for a method of regenerating beta-cells of pancreas. An exemplary method for increasing the capacity of insulin producing cells ($\beta$ cells of Islets of Langerhans) in humans and animals is administering a therapeutically effective dose of a composition of an extract of *Costus pictus D. Don*. The extract can be administered to a mammal for a method for increasing the capacity of insulin producing cells of the mammal to become more effective insulin producers. The extract can be administered to a mammal for a method for increasing the capacity of insulin producing cells, whereby damaged beta-cells present in the pancreas regenerate into insulin producing cells. The extract can be administered to a mammal for a method of controlling normal liver glycogen in the mammal. An innovative method, technique and treatment to regenerate beta cells of pancreatic islets includes administering an extract of *Costus pictus D. Don* in the dose of 50-200 mg/kg/day in streptozotocin induced diabetic rats and such other mammals and also extendable to humans in applicable dosages including a dosage of 500-2000 mg/day for humans. The disclosure provides ecofriendly and value engineered methods for preparing an effective extract from plant *Costus pictus D. Don* to obtain optimum glycemic control.

In some embodiments of the method of inducing hypoglycemia, a dose of the extract of about 500 mg/day to about 2000 mg/day is administered to a human. In some embodiments of the method of regenerating beta-cells of pancreas, a dose of the extract of about 500 mg/day to about 2000 mg/day is administered to a human. In some embodiments of the method for increasing the capacity of insulin producing cells (β cells of Islets of Langerhans) in a human, a dose of the extract of about 500 mg/day to about 2000 mg/day is administered to a human. In some embodiments of the method for increasing the capacity of insulin producing cells in a human, whereby damaged beta-cells present in the pancreas regenerate into insulin producing cells, a dose of the extract of about 500 mg/day to about 2000 mg/day is administered to a human. In some embodiments of the method of controlling normal liver glycogen in the mammal, a dose of the extract of about 500 mg/day to about 2000 mg/day is administered to a human.

The disclosure provides methods for long term management of diabetes by avoiding the problems associated with tight control of blood glucose concentrations, i.e., hypoglycemia tolerance and seizures, while simultaneously avoiding the problems associated with conventional moderate control of blood glucose concentrations, i.e., pathological complications associated with hyperglycemia, such as nephropathy, retinopathy etc.

In some embodiments, the extract can be effectively mixed with other herbal/nutraceutical/synthetic components without losing its objectivity.

The disclosure provides a path breaking method wherein the innovative medicinal preparation of *Costus pictus D. Don* is obtained by using low molecular weight alcohols, as such or mixed with water, halogenated hydrocarbons, organic ethers, low molecular weight esters, other organic solvents and low molecular weight ketones. The disclosure provides methods for preparing extracts of *Costus pictus D. Don*. An exemplary method of preparing an extract of *Costus pictus D. Don* includes collecting a starting material of *Costus pictus D. Don*; treating the starting material with low molecular weight alcohols, low molecular weight alcohols mixed with water, halogenated hydrocarbons, organic ethers, low molecular weight esters, alkanes, other organic solvents, low molecular weight ketones, water or combinations thereof to prepare a mixture; and processing the mixture to prepare the extract. The starting material includes a fresh whole plant of *Costus pictus D. Don*, fresh leaves of *Costus pictus D. Don*, dried leaves of *Costus pictus D. Don*, and combinations thereof.

Low molecular weight alcohols that can be used in preparation of the extract include methanol, ethanol, isopropanol, n-butanol and combinations thereof. Halogenated hydrocarbons that can be used for extract preparation include methylene chloride, ethylene dichloride, chloroform, and combinations thereof. Esters that can be used for extract preparation include methyl acetate, ethyl acetate, propyl acetate, n-butyl acetate and combinations thereof. Ketones that can be used for extract preparation include acetone, methyl ethyl ketone, and combinations thereof. Alkanes that can be used for preparation of the extract include pentane, hexane, heptane, isooctane, and combinations thereof.

An exemplary method of preparing an extract using fresh leaves of *Costus pictus D. Don* as the starting material is provided in FIG. 1. In FIG. 1, fresh leaves of *Costus pictus D. Don* are subjected to extraction with methanol to obtain a mixture. The mixture is filtered to obtain a filtrate and a residue (Residue I). The filtrate is the methanol soluble fraction (Fraction I or Fr. I). Fraction I is concentrated and dried to obtain an extract. The extract Fraction I is reextracted with hexane to obtain a mixture. The hexane containing mixture is filtered to obtain a filtrate, which is a hexane soluble fraction (Fraction II or Fr. II), and a residue (Residue II). Next Residue II is further extracted with ethyl acetate to form a mixture. The ethyl acetate containing mixture is filtered resulting in a filtrate, which is an ethyl acetate soluble fraction (Fraction III or Fr. III), and a residue (Residue III). The Residue III is extracted with butanol to prepare a mixture. The butanol containing mixture is filtered resulting in a filtrate, which is a butanol soluble fraction (Fraction IV or Fr. IV), and a residue fraction, namely Fraction V. Fractions II, III, IV and IV are concentrated and dried to obtain extracts. The dried extracts are dissolved in water or other suitable solvents to test for hypoglycemic activity in mammals.

An exemplary method of preparing an extract of *Costus pictus D. Don* includes collecting a starting material comprising *Costus pictus D. Don*; refluxing the starting material with a first low molecular weight alcohol to prepare a mixture I; filtering the mixture I to prepare a filtrate I and a residue I; concentrating the filtrate I to prepare a concentrate I; and drying the concentrate I to prepare a fraction I, wherein the starting material includes a fresh whole plant of *Costus pictus D. Don*, fresh leaves of *Costus pictus D. Don*, dried leaves of *Costus pictus D. Don*, or combinations thereof, and wherein the fraction I is designated as the extract.

An exemplary method of preparing an extract includes treating fraction I with an alkane to prepare a mixture II; filtering the mixture II to prepare a filtrate II and a residue II; concentrating the filtrate II to prepare a concentrate II; and drying the concentrate II to form a fraction II, wherein the fraction II is designated as the extract.

An exemplary method of preparing an extract includes treating residue II with a low molecular weight ester to prepare a mixture III; filtering the mixture III to prepare a filtrate III and a residue III; concentrating the filtrate III to prepare a concentrate III; and drying the concentrate III to form a fraction III, wherein the fraction III is designated as the extract.

An exemplary method of preparing an extract includes treating residue III with a second low molecular weight alcohol to prepare a mixture IV; filtering the mixture IV to prepare a filtrate IV and a residue (fraction V), wherein the residue (fraction V) is designated as the extract. An exemplary method of preparing an extract includes concentrating filtrate IV to prepare a concentrate IV; and drying the concentrate IV to form a fraction IV, wherein the fraction IV is designated as the extract.

In an exemplary method of preparing the extract the first low molecular weight alcohol is mixed with water.

An exemplary method of preparing an extract includes collecting fresh leaves of *Costus pictus D. Don*, cleaning the fresh leaves to prepare cleaned leaves, drying the cleaned leaves to prepare dried leaves, powdering the dried leaves to prepare a dried powder. In an exemplary method of preparing the extract, the dried powder is refluxed with the first low molecular weight alcohol to prepare an extract.

First low molecular weight alcohols that can be used for preparing an extract include methanol, ethanol, isopropanol, and combinations thereof.

Second low molecular weight alcohols that can be used for preparing an extract include methanol, ethanol, propanol, n-butanol, and combinations thereof.

Low molecular weight esters that can be used for preparing an extract include methyl acetate, ethyl acetate, propyl acetate, n-butyl acetate and combinations thereof.

Alkanes that can be used for preparing an extract include pentane, hexane, heptane, isooctane, and combinations thereof.

In an exemplary method of preparing the extract, the starting material of *Costus pictus D. Don* is a fresh whole plant of *Costus pictus D. Don*. In an exemplary method of preparing the extract, the starting material is fresh leaves of *Costus pictus D. Don*. In an exemplary method of preparing the extract, the starting material is dried leaves of *Costus pictus D. Don*. In an exemplary method of preparing the extract, the starting material is a combination of two or more of fresh plant of *Costus pictus D. Don*, fresh leaves of *Costus pictus D. Don* and dried leaves of *Costus pictus D. Don*.

INDUSTRIAL APPLICATION OF INVENTION

Accordingly it is an object of this invention to provide an improved method of preparing a substance for treating diabetes mellitus.

Another object of the present invention is to provide methods of treatment for controlling/preventing type I and type II diabetic patients without side effects.

A feature of present invention is to regenerate pancreatic beta cells and obtain optimum glycemic control in human beings.

It will be readily understood by the skilled artisan that numerous alterations may be made to the examples and instructions given herein including the generation of different DP IV inhibitors and alternate therapeutic compositions without departing from either the spirit or scope of the present invention. These and other objects and features of present invention will be made apparent from the following examples. The following examples as described are not intended to be construed as limiting the scope of the present invention.

EXAMPLES

Example 1

Preparation of Dry Powder

Fresh leaves of *Costus pictus* were collected, cleaned and dried under shade. The dried leaves were powdered and kept as dried powder.

Example 2

Preparation of Extract

An extract of *Costus pictus D. Don* was prepared according to the procedure shown in FIG. 1. Fresh leaves of *Costus pictus D. Don* was refluxed with 90% methanol for four hours. After refluxing the mixture was filtered and filtrate was concentrated and dried (fraction I or Fr. I). This extract was fractionated with different solvents like hexane, ethyl acetate and butanol. The fraction II or Fr. II (hexane part), fraction III or Fr. III (ethyl acetate part), fraction IV or Fr. IV (butanol part) and fraction V or Fr. V (residue) were concentrated and dried under vacuum. The hexane soluble fraction (II) was discarded. The residue was extracted with ethylacetate. The fractions I, III, IV and V were screened for hypoglycemic activity.

Example 3

Activity of different extracts were tested using Sprague dawley rats of either sex aged 3 months weighing 180-200 g. After 3-4 hrs of fasting the rats were divided into 7 groups of 6 in each, one group kept as control and 4 groups were given different fractions (Fraction I, Fraction III, Fraction IV and Fraction V) of extract in the dose of 100 mg/kg. Sixth and seventh groups were given standard drugs glybenclamide (1 mg/kg) and metformin (150 mg/kg) respectively.

Figure 2:
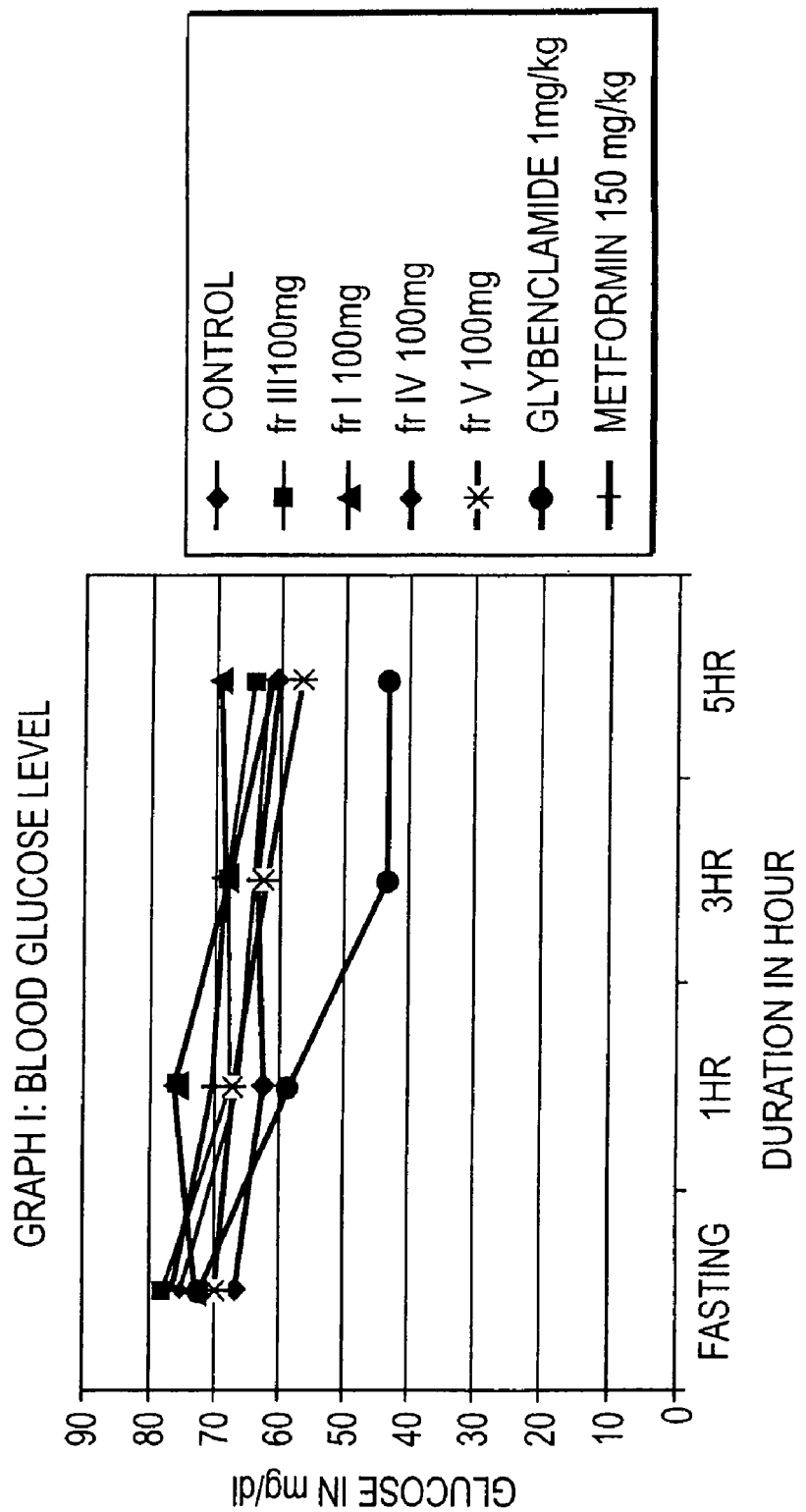
FIG. 2 provides a graph showing blood glucose level in untreated normal rats (control); normal rats treated with various fractions, namely, Fraction I (fr I), Fraction III (fr III), Fraction IV (fr IV) and Fraction V (fr V); normal rats treated with glybenclamide and metformin. The x-axis provides duration in hrs after feeding extract to fasting normal rats. The y-axis provides blood glucose concentration in mg/dl.

As seen in Table 2 and the graph in FIG. 2, results of the study showed that administration of fraction III (ethyl acetate part, shown in FIG. 1) and fraction V (residue, shown in FIG. 1) in the dose of 100 mg/kg significantly ($p<0.05$) decreased the blood glucose level after five hours. In the case of standard drug glybenclamide there was significant ($p<0.05$) decrease in blood glucose level in the first hour and effect was more pronounced in the third and fifth hour. Metformin however produced significant ($p<0.05$) decrease in blood glucose level in the fifth hour. (See Table II, graph I) The extract/drug was administered orally (single dose) after 4 hours of fasting. Fraction III (ethyl acetate fraction) and fraction V (residue) showed significant decrease ($p<0.05$) in blood glucose level after 5 hours after extract feeding. Standard drug glybenclamide produced significant ($p<0.05$) decrease in blood glucose level in the first hour itself, while metformin produced significant decrease ($p<0.05$) in the fifth hour. In FIG. 2, the graph provides blood glucose level in normal rats in mg/dl measured over a duration of 5 hours. The normal rats were fed with different fractions of the extract after four hours of fasting. The graph shows that administration of Fraction III and Fraction V produced a significant decrease in blood glucose level after 5 hours.

TABLE 2

Effect of different fractions of extract of *Costus pictus D. Don* on blood sugar level (mg/dl) in normal rats.

| Group | Dosage/kg | Fasting | 1 hr | 3 hr | 5 hr |
|---|---|---|---|---|---|
| Control | 1 ml distilled water | 75.3 ± 5.4 | 65.6 ± 4.2 | 64.0 ± 4.3 | 62.0 ± 3.3 |
| Fraction I | 100 mg | 73.5 ± 0.6 | 76.8 ± 2.8 | 68.5 ± 4.5 | 69.5 ± 4.6 |
| Fraction III | 100 mg | 78.8 ± 3.5 | 68.1 ± 4.8 | 68.0 ± 5.3 | *63.8 ± 5.6 |
| Fraction IV | 100 mg | 67.1 ± 2.2 | 62.5 ± 3.1 | 63.3 ± 2.7 | 60.5 ± 1.9 |
| Fraction V | 100 mg | 70.3 ± 4.3 | 67.3 ± 1.0 | 62.0 ± 2.0 | *57.0 ± 2.3 |
| Glybenclamide | 1 mg | 72.6 ± 8.6 | *58.8 ± 9.8 | *43.3 ± 8.2 | *43.2 ± 5.8 |
| Metformin | 150 mg | 76.6 ± 4.1 | 70.6 ± 3.0 | 68.3 ± 2.6 | *61.5 ± 3.0 |

The most active fraction, i.e., ethyl acetate fraction (fraction III) was taken for further animal experiments and human trials.

Example 4

Glucose tolerance study of extract of *Costus pictus D. Don* was conducted in normal Sprague dawley rats. After acclimatization period, rats were divided into five groups—one group (Group A) kept as control and remaining four groups (Group B, Group C, Group D and Group E) as experimental groups. Fasting blood glucose was noted and experimental animals was administered the extract (ethyl acetate fraction) orally in the dose of 50 mg (Group B), 100 mg (Group C), 200 mg (Group D), and 1 g/kg (Group E). Glucose was administered orally in the dose of 1 g/kg for all animals one hour after extract administration. Blood sugar was tested at an interval of half hour, 1 hour, 2 hour, 3 hour and 5 hour by the method of Asatoor and King.

Figure 3:
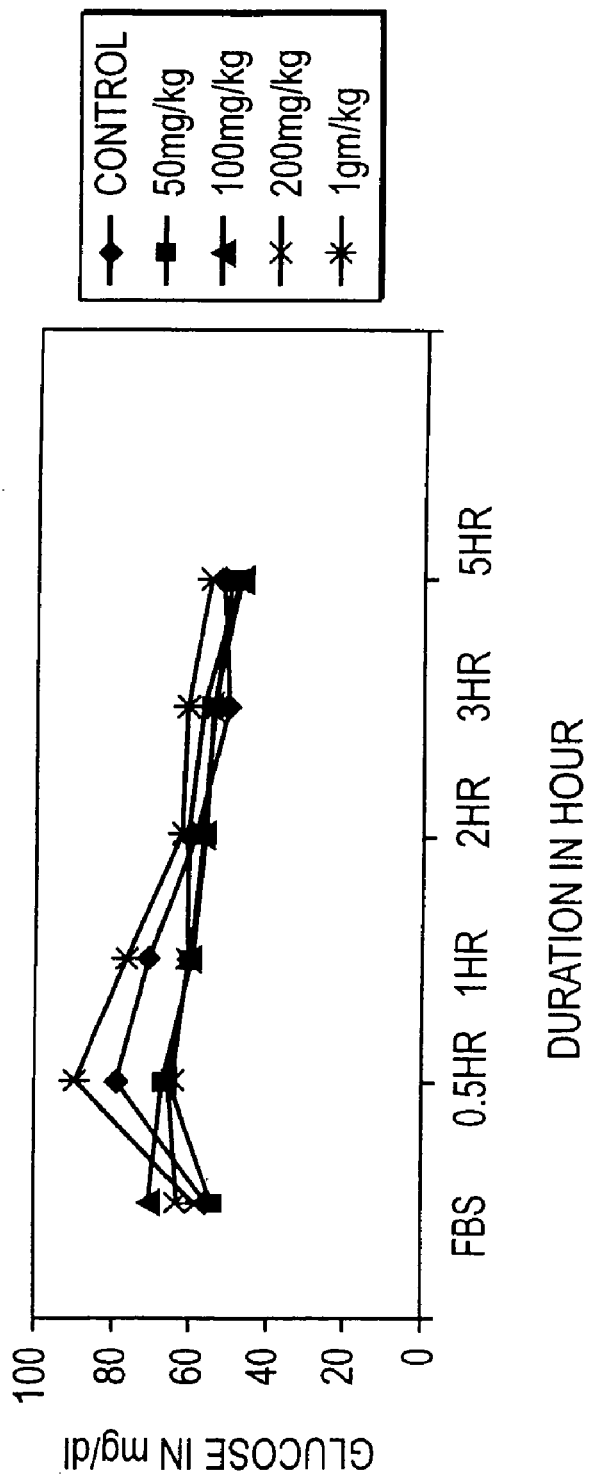
FIG. 3 provides a graph showing glucose tolerance test in normal rats, which include untreated (control) rats, normal rats treated with 50 mg/kg (amount of extract/body weight of rat), normal rats treated with 100 mg/kg, normal rats treated with 200 mg/kg and normal rats treated with 1 gm/kg. The x-axis provides duration in hrs, wherein the zero hrs refers to the fasting blood sugar level (FBS). The y-axis provides blood sugar level in mg/dl.

Results of glucose tolerance test using different doses of the above said extract showed that doses of 100 mg/kg and 200 mg/kg inhibited the initial peak rise in blood glucose and produced significant (p<0.05) decrease in blood glucose level within 3 hrs after glucose administration (Table 3, FIG. 3). Oral administration of extract in the dose of 100 mg and 200 mg/kg produced significant (p<0.05) decrease in the 3rd and 5th hour in normal rats. The dosages 50 mg/kg and 1 g/kg did not produce any significant effect. The results of the glucose tolerance test in normal rats are depicted graphically in FIG. 3. FIG. 3 shows that administration of extract of *Costus pictus D. Don* in the dose of 100 mg/kg and 200 mg/kg produced significant decrease in blood glucose within 3 hrs after glucose loading.

(Group B, "Str+ ext") was given the above extract in the dose of 100 mg/kg and second group (Group C, "Str") maintained as untreated diabetic control. Another group was administered distilled water served as the normal control group (Group A). After 35 days of oral treatment of extract these animals were subjected to glucose tolerance test along with normal control group (Group A).

Figure 4:
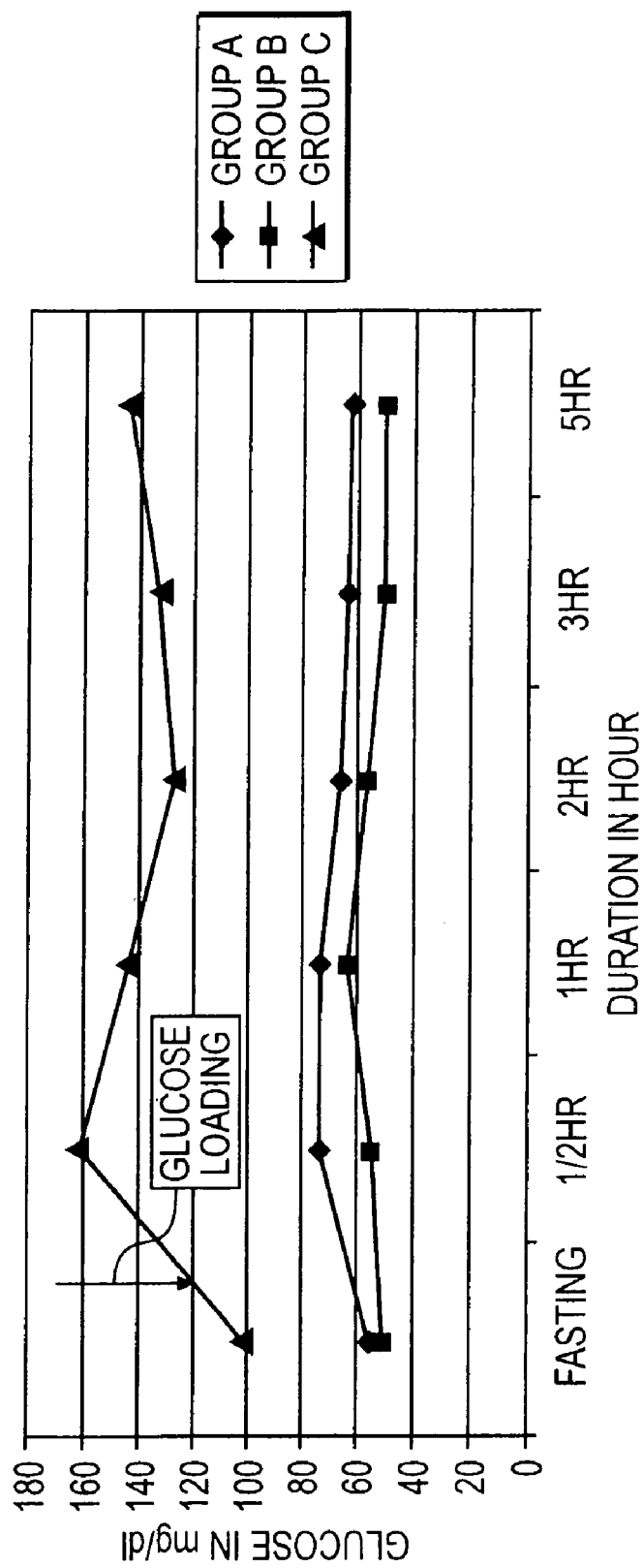
FIG. 4 provides a graph showing glucose tolerance test in diabetic rats. Group A were untreated normal rats (control), Group B were rats treated with streptozotocin to induce diabetes followed by treatment with extract and Group C refers were rats treated with streptozotocin but not with extract. The x-axis provides duration in hours over which the blood glucose concentration was monitored. The y-axis shows blood glucose concentration in mg/dl. The arrow indicates the time of glucose loading in the rats.

Glucose tolerance test (GTT) results provided in Table 4 and graph in FIG. 4 show that in untreated diabetic control animals, blood glucose increased to a significant (p<0.05) level within half an hour after glucose administration and remained significantly high throughout the experimental period. In the extract treated diabetic rats, there was inhibition of initial hyperglycemia and blood glucose returned to baseline level within three hours after glucose administration similar to normal control rats. Extract administration prevented initial hyperglycemia and blood sugar level became normal within three hours, while in untreated diabetic control blood sugar level increased to a significant level and remained high throughout the experimental period. In FIG. 4, the graph shows glucose tolerance test in diabetic rats, wherein glucose concentration in blood in mg/dl was measured over a duration

TABLE 3

Effect of extract of *Costus pictus* D. Don on GTT (glucose tolerance test) in normal rats.

| group | dosage | Fasting (mg/dl) | Glucose administration after 1 hr after extract administration | | | | |
|---|---|---|---|---|---|---|---|
| | | | ½ hr (mg/dl) | 1 hr (mg/dl) | 2 hr (mg/dl) | 3 hr (mg/dl) | 5 hr (mg/dl) |
| Group A | 1 ml distilled water | 55.4 ± 5.4 | 79.0 ± 6.05 | 71 ± 2.9 | 58.0 ± 3.8 | 50.3 ± 4.1 | 52.2 ± 4.8 |
| Group B | 50 mg/kg | 53.7 ± 5.2 | 66.2 ± 3.4 | 59.5 ± 2.4 | 55.8 ± 3.3 | 53.5 ± 0.9 | 49.8 ± 1.2 |
| Group C | 100 mg/kg | 70.5 ± 3.6 | 66.5 ± 1.9 | 60.8 ± 2.4 | 61.5 ± 1.1 | *57.0 ± 3.9 | *47.7 ± 4.3 |
| Group D | 200 mg/kg | 62.8 ± 3.5 | 63.7 ± 2.6 | 60.3 ± 2.4 | 57.0 ± 1.6 | *52.2 ± 1.7 | *47.8 ± 1.2 |
| Group E | 1 g/kg | 58.8 ± 3.0 | 89.3 ± 10.2 | 76.3 ± 7.8 | 62.2 ± 5.7 | 61.0 ± 7.0 | 54.8 ± 1.2 |

Example 5

Glucose tolerance study of extract of *Costus pictus D. Don* was conducted in experimental diabetic rats. Diabetes was induced by injecting Streptozotocin (50 mg/kg—intraperitoneally) and they were divided into two groups. One group of 5 hrs. The results show that oral administration of 100 mg/kg of *Costus pictus D. Don* prevented hyperglycemia in diabetic rats (Group B). Whereas after glucose loading, the blood glucose increased significantly throughout the experimental period in the untreated diabetic control rats (Group C).

TABLE 4

Effect of extract of *Costus pictus* D. Don on GTT in Diabetic and Treated Rats

| Groups | Fasting (mg/dl) | Glucose administration (1 g/kg) 1 hr after extract administration | | | | |
|---|---|---|---|---|---|---|
| | | ½ hr (mg/dl) | 1 hr (mg/dl) | 2 hr (mg/dl) | 3 hr (mg/dl) | 5 hr (mg/dl) |
| Group A (control) | 54.4 ± 3.1 | 75.5 ± 4.8 | 73.3 ± 3.1 | 65.5 ± 3.1 | 63.7 ± 1.7 | 62.2 ± 2.1 |
| Group B (Str + ext) | 51.6 ± 4.5 | 55.2 ± 5.9 | 63.2 ± 8.1 | 57.0 ± 5.5 | 50.4 ± 2.1 | 50.4 ± 4.2 |
| Group C (Str) | 104.2 ± 20.7 | *164.0 ± 52.2 | *146.0 ± 41.6 | *129.4 ± 41.1 | *135.0 ± 46.6 | *144.8 ± 44.9 |

Example 6

Hypoglycemic action of extract of *Costus pictus* D. Don were tested in Streptozotocin (50 mg/kg) induced diabetic rats of Sprague dawley strain of either sex. They were randomly assigned to three groups—(A) control group, (B) extract treated group and (C) untreated diabetic control. Diabetes was induced in Groups B and C by an injection of streptozotocin for 10 days.

Blood was collected from the caudal vein under light ether anaesthesia after an overnight fasting. Blood glucose was estimated (Asatoor & King) before starting the experiment and repeated every 7 days for 5 weeks. Liver glycogen was estimated in all animals after sacrificing the animals. Pancreas from the animals were processed for histological studies. Body weight of all animals were noted before and every 10 days during administration of extract.

Figure 5:
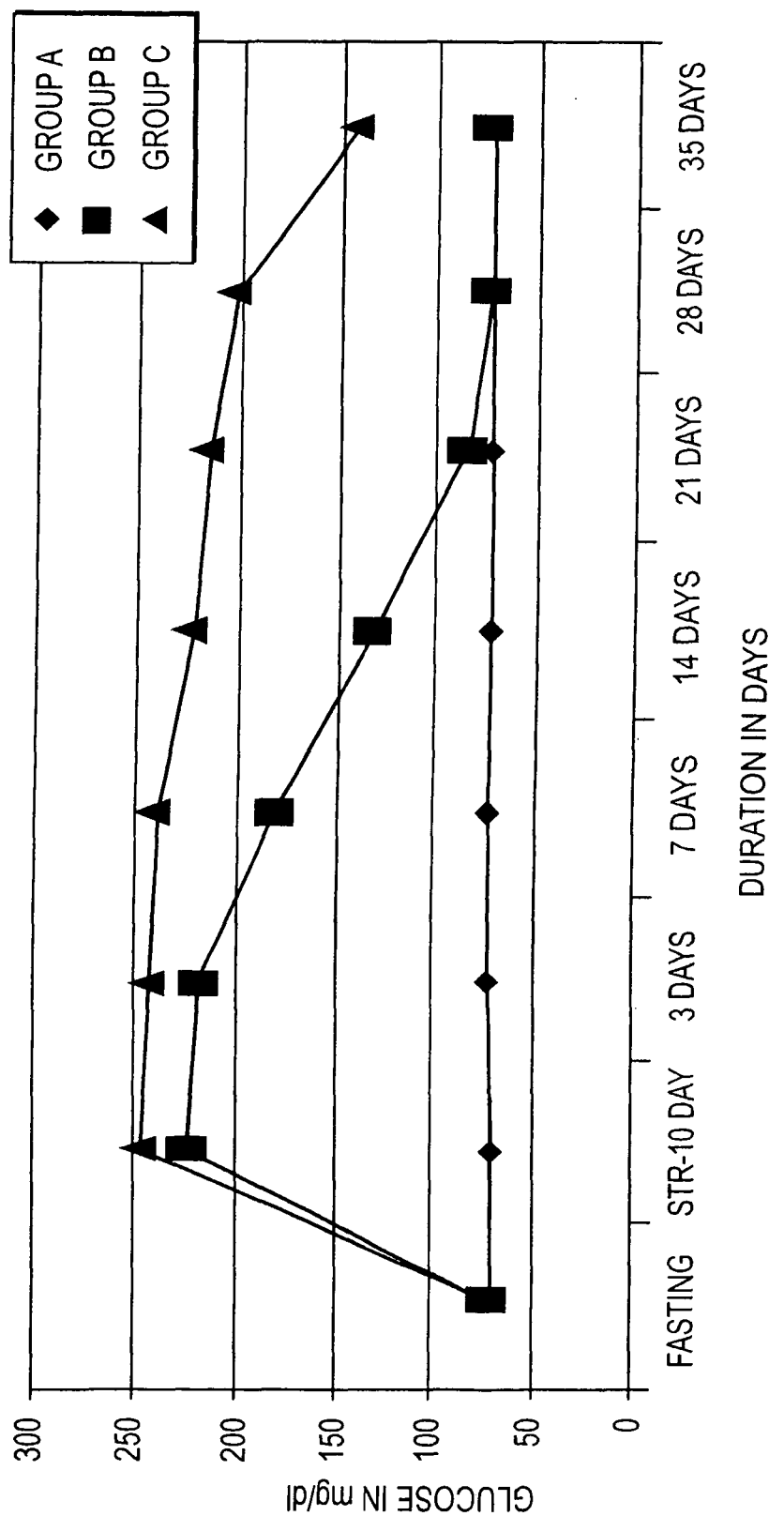
FIG. 5 provides a graph showing effect of extract administration on blood glucose level. Group A were untreated normal rats (control), Group B were rats treated with streptozotocin to induce diabetes followed by treatment with extract, and, Group C refers were rats treated with streptozotocin but not with extract. The x-axis shows the duration in days over which the glucose level was monitored. The y-axis shows blood glucose concentration in mg/dl.

Results in Table 5 and graph in FIG. 5 show that blood glucose level remained same throughout the experimental period in control rats. There was a significant increase in blood sugar level in group B and C which were given streptozotocin. Administration of extract (100 mg/kg orally) produced decrease in blood glucose level within three days itself, but not to a significant level. Seven days treatment produced significant decrease ($p<0.05$) in blood glucose level, and twenty eight days treatment brought the blood glucose to baseline level. Further treatment did not produce hypoglycemia. Blood glucose level remained in hyperglycemic state in group C (untreated diabetic rats), throughout the experimental period. Table 5 and graph in FIG. 5 show that extract administration caused a significant decrease ($p<0.05$) in blood glucose level by 7 days treatment, glucose became normal within 28 days treatment and further treatment did not produce hypoglycemia. In untreated diabetic rats blood sugar level remained high compared to the treatment group throughout the study period. The graph in FIG. 5 shows that oral administration of extract of *Costus pictus* D. Don (100 mg/kg) significantly decreased glucose level in streptozotocin induced diabetic rats (group B), whereas in untreated diabetic control (group C) blood glucose remained significantly higher throughout the experimental period.

Figure 6:
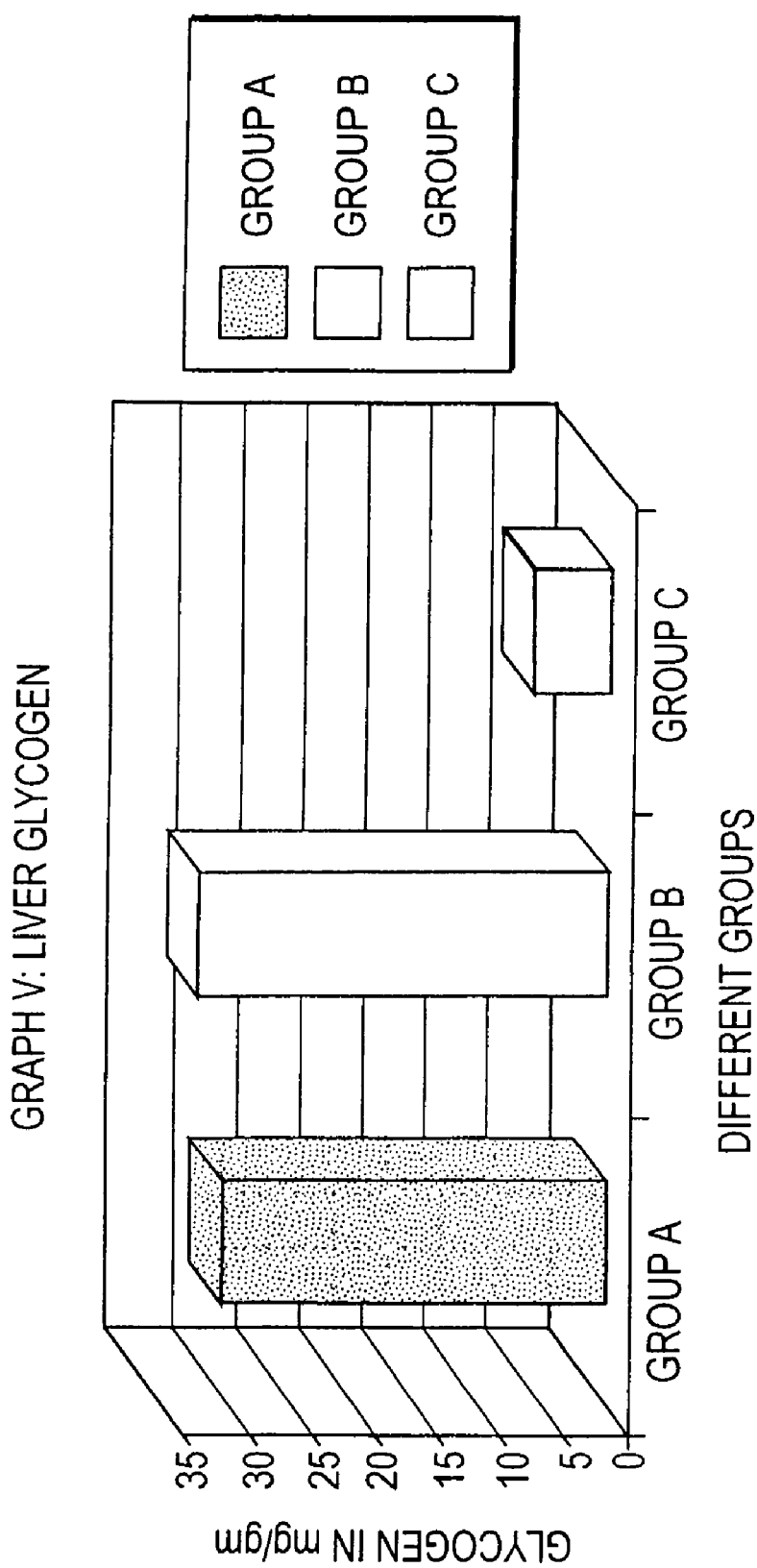
FIG. 6 provides a graph showing effect of extract administration on levels of liver glycogen. Group A were untreated normal rats (control), Group B were rats treated with streptozotocin to induce diabetes followed by treatment with extract and Group C refers were rats treated with streptozotocin but not with extract. The x-axis provides the different groups. The y-axis provides glycogen level in mg/gm.

Liver glycogen level in extract (100 mg/kg) treated groups was same as in normal control rats. But there was significant decrease ($p<0.05$) in glycogen level in untreated diabetic control rats. See Table 6 and graph in FIG. 6. Low liver glycogen in group C (untreated diabetic rats) showed decreased conversion of blood glucose to liver glycogen in the diabetic rats due to absence of insulin. The extract seems to increase the conversion of glucose to glycogen in the liver of diabetic rats. Table 6 shows that liver glycogen level in untreated diabetic control rats significantly ($p<0.05$) decreased, while in the treatment group glycogen level was brought back to normal as in control group. The graph in FIG. 6 shows significantly ($p<0.05$) lower liver glycogen level in untreated diabetic control (group C) than normal (group A) and treatment group (group B).

TABLE 6

Effect of extract of *Costus pictus* D. Don on liver glycogen at the end of treatment period.

| Group A (control) | Group B (Str + ext) | Group C (Str) |
|---|---|---|
| 30.5 ± 0.3 | 32.3 ± 1.1 | *6.0 ± 1.4 |

Histopathological studies showed decreased number of islets of langerhans and decreased numbers of beta cells per islets in the untreated diabetic control compared to normal or extract treated groups. In diabetic rats varying degrees of cellular damage was seen in the islets. There was decrease in population of cells with nuclear pyknosis, karyorerrhsis and karyolysis with degranulation and cytolysis. In treatment group the degree of cellular damage was lesser and regeneration was observed. Compared to normal rats, there was 75% decrease in number of cells in untreated diabetic control, while in treatment group there was only 29% decrease. Table 7 shows that treatment of diabetic rats with extract showed regeneration of pancreatic beta cells in Islets, while in untreated diabetic control number of beta cells was less.

TABLE 5

Effect of extract of *Costus pictus* D. Don on streptozotocin (50 mg/kg) induced diabetic rats

| Groups | Fasting | 10 days after streptozotocin injection | 3 days | 7 days | 14 days | 21 days | 28 days | 35 days |
|---|---|---|---|---|---|---|---|---|
| | | | | Treatment period | | | | |
| Group A (control) | 72.1 ± 5.3 | 70.0 ± 3.4 | 72.0 ± 3.0 | 73.1 ± 4.2 | 72.7 ± 3.1 | 73.0 ± 4.1 | 73.7 ± 4.1 | 72.2 ± 3.8 |
| Group B (Str + ext) | 72.0 ± 3.8 | *223.0 ± 20.9 | 219.0 ± 20.1 | *179.1 ± 20.6 | *131.0 ± 18.2 | *85.0 ± 7.4 | *73.0 ± 6.0 | *73.0 ± 4.0 |
| Group C Str | 70.0 ± 4.8 | 249.0 ± 26.1 | 246.0 ± 26.6 | 243.0 ± 26.7 | 226.9 ± 25.4 | 217.0 ± 25.0 | 207.0 ± 21.0 | 141.0 ± 19.4 |

TABLE 7

Effect of extract of Costus pictus D. Don treatment on number of beta cells per pancreatic islets in experimental rats

| Group | No. of beta cells/islets | Effect of treatment on pancreatic cells compared to normal (percentage) |
|---|---|---|
| Normal | 139 ± 17.4 | |
| Treatment group | 98 ± 21.5 | 29% |
| Untreated diabetic control | 34 ± 8.5 | 75% |

Figure 7:
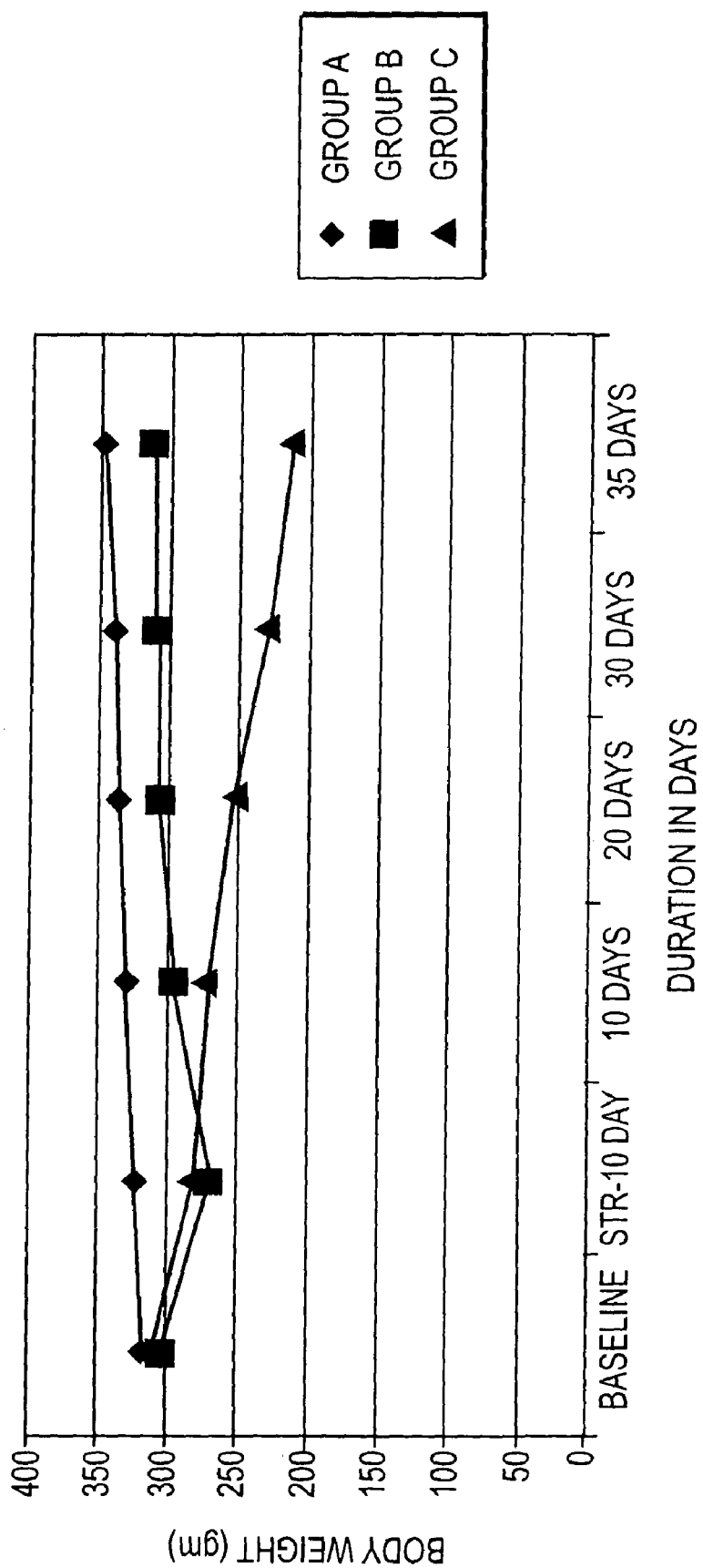
FIG. 7 provides a graph showing the effect of extract administration on body weight of rats. Group A were untreated normal rats (control), Group B were rats treated with streptozotocin to induce diabetes followed by treatment with extract and Group C refers were rats treated with streptozotocin but not with extract. The x-axis provides the time interval over which body weight was monitored. The y-axis provides body weight in gm.

Table 8 shows that administration of extract in the dose of 100 mg/kg inhibited the weight loss in diabetic rats (group B) even by 10$^{th}$ day and weight was brought back to baseline level by 20$^{th}$ day of treatment. Rats administered with distilled water served as control (Group A) did not exhibit any weight loss. In untreated diabetic control (Group C) the body weight was significantly lower than normal control. The graph in FIG. 7 shows that administration of extract of *Costus pictus* D. Don brought the body weight to normal level within 20 days treatment in group B, while body weight remained significantly lower in group C.

TABLE 8

Effect of extract of Costus pictus D. Don on body weight (grams) in different groups of rats

| Groups | Baseline | 10 days after Str | Treatment period | | | |
|---|---|---|---|---|---|---|
| | | | 10 days | 20 days | 30 days | 35 days |
| Group A | 318.6 ± 10.5 | 323 ± 9.5 | 332 ± 11.1 | *337 ± 11.1 | *342.5 ± 10.7 | *347.5 ± 9.8 |
| Group B | 305.3 ± 7.0 | *272.0 ± 6.6 | 296.5 ± 10.8 | 309.8 ± 8.0 | 313.2 ± 8.9 | 305.0 ± 7.5 |
| Group C | 314.8 ± 11.6 | *285.5. ± 8.6 | *272.6 ± 10.1 | *255.5 ± 9.2 | *233.8 ± 9.8 | *222.8 ± 11.2 |

Example 7

Acute toxicity study of extract of *Costus pictus* D. Don were tested in Swiss albino mice of both sexes. The mice divided into three groups of six in each. Group A was kept as control group and remaining 2 groups (B and C) were used for experiment. Group A mice were given distilled water (0.25 ml/25 g body weight) and groups B and C were given 0.25 ml extract per 25 g mice in the dosage of 100 mg and 200 mg/Kg body weight orally and observed continuously for first six hours. Mortality was recorded for 15 days. (See Ghosh, 1970)

The extract was non-toxic even up to 200 mg/kg given orally to albino mice. All animals behaved normally. No neurological or behavioural effects were noted. No mortality was recorded in 15 days. This study showed that oral feeding of extract of *Costus pictus* D. Don even up to 200 mg/kg did not produce any acute toxic effects in mice.

Example 8

Effect of extract of *Costus pictus* D. Don was tested in a normal healthy female subject (52 yrs). After estimating fasting blood glucose, 500 mg of extract (I capsule) was given to normal subject, before breakfast. Blood sugar was estimated after 2 hr, 5 hr and subject was allowed to take normal diet. Fasting blood glucose was estimated after 24 hr also. (See Table 9 and graph in FIG. 8)

Figure 8:
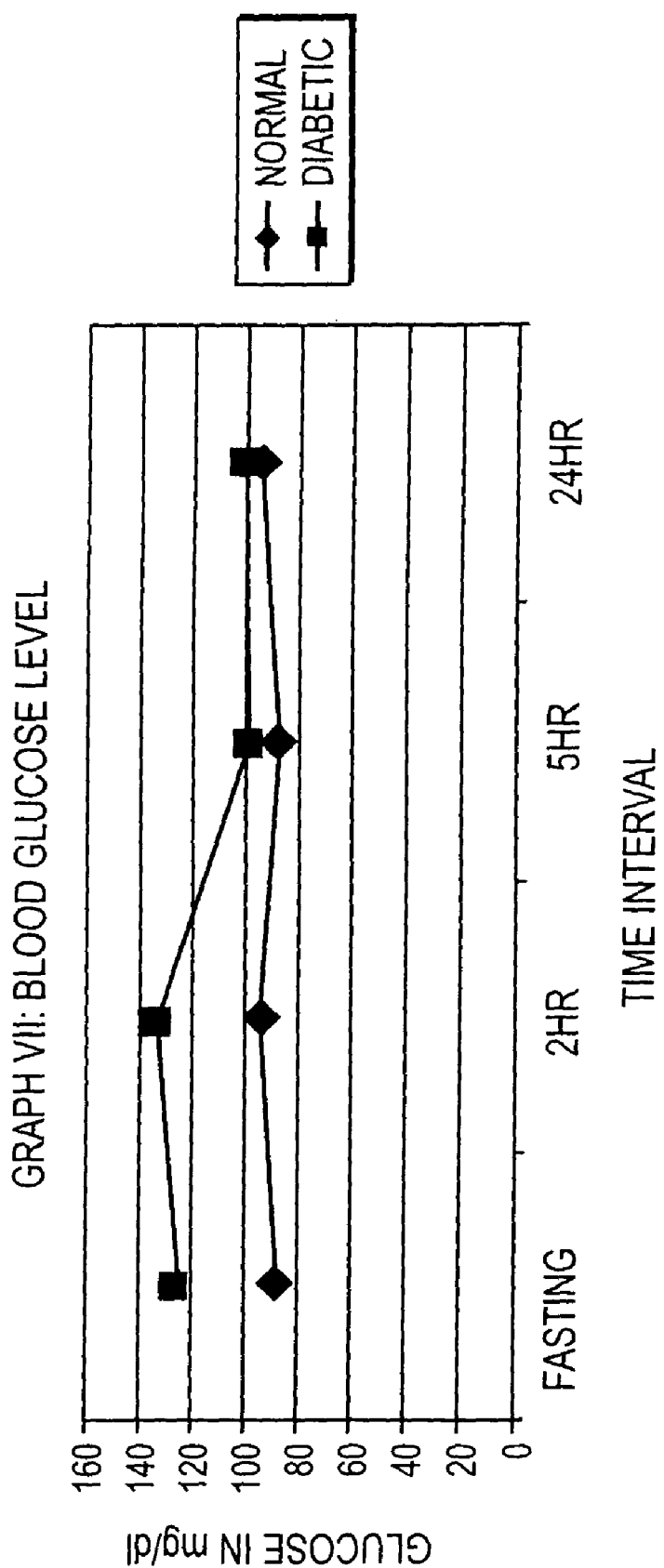
FIG. 8 provides a graph showing the effect of extract administration on blood glucose level in a normal and in a diabetic human. The x-axis provides the time interval over which blood glucose was monitored. The y-axis provides glucose concentration in mg/dl.

Results provided in Table 9 and graph in FIG. 8 showed that capsule did not have any significant effect on normal subject. Table 9 shows that administration of 500 mg of extract (single dose) did not produce any significant effect on blood glucose level in normal subject.

TABLE 9

Effect of 500 mg extract (1 capsule - single dose) of Costus pictus D. Don on blood glucose (mg/dl) level in normal Human being

| subject | Fasting | Capsule + breakfast | | normal diet |
|---|---|---|---|---|
| | | 2 hr | 5 hr | 24 hr |
| normal (1) | 88 | 95 | 88 | 95 |

Example 9

Effect of extract of *Costus pictus* D. Don was tested in diabetic patients (45-52 yrs). After estimating fasting blood glucose, 500 mg of extract (I capsule) was given to patient, before breakfast. Blood sugar was estimated after 2 hr, 5 hr and patients were allowed to take normal diet. Fasting blood glucose was estimated after 24 hr also.

Table 10 shows that administration of 500 mg extract (single dose) produced significant effect on blood glucose level in diabetic patient. Result showed significant lowering of blood glucose from the 2nd hour onwards, which reached maximum on 5th hour period in diabetic subjects. Results are also provided in the graph in FIG. 8. FIG. 8 shows the effect of 500 mg of extract of *Costus pictus* D. Don (single dose) on normal (group A) and diabetic (group B) human beings.

TABLE 10

Effect of 500 mg extract (1 capsule - single dose) of Costus pictus D. Don on blood glucose (mg/dl) level in diabetic patients

| subject | fasting | Capsule + breakfast | | normal diet |
|---|---|---|---|---|
| | | 2 hr | 5 hr | 24 hr |
| Diabetics(5) | 130.7 ± 1 | 144.3 ± 26.1 | 98.7 + 5.3 | 100 ± 12.5 |

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A method of controlling glycogen levels in a mammal, the method comprising administering an extract of *Costus pictus*.

2. The method of claim 1 comprising administering a 90% methanol extract of fresh leaves of *Costus pictus*.

3. The method of claim 1 comprising administering the extract of *Costus pictus* at a dose of about 500 mg/day to about 2000 mg/day.

4. The method of claim 1 comprising administering the extract of *Costus pictus* at a dose of about 500 mg/day.

5. The method of claim 1, wherein the extract of *Costus pictus* is administered in a dosage form selected from the group consisting of capsule, tablet, granule, sachet, powder, paste, ointment, infusion, injection, ampoule, solution, suspension, emulsion, pill, sustained release formulation and combinations thereof.

6. The method of claim 1, wherein the mammal is a human.

7. The method of claim 6, wherein the human is a diabetic patient.

8. The method of claim 6, wherein the human has hyperglycemia.

9. A method of controlling glycogen levels in a mammal, the method comprising administering dried leaves of *Costus pictus*, dried powder of *Costus pictus*, or, juice of fresh leaves of *Costus pictus* to the mammal in need thereof.

10. The method of claim 9, wherein the mammal is a human.

11. The method of claim 10, wherein the human is a diabetic patient.

12. The method of claim 10, wherein the human has hyperglycemia.

* * * * *